United States Patent [19]

Mita et al.

[11] Patent Number: 4,605,759
[45] Date of Patent: Aug. 12, 1986

[54] PROCESS FOR PRODUCTION OF β-PHENYLSERINE

[75] Inventors: Ryuichi Mita; Toshio Katoh, both of Kawasaki; Chojiro Higuchi; Akihiro Yamaguchi, both of Kamakura, all of Japan

[73] Assignee: Mitsui Toatsu Chemicals, Inc., Tokyo, Japan

[21] Appl. No.: 636,289

[22] Filed: Jul. 31, 1984

[30] Foreign Application Priority Data

Aug. 1, 1983 [JP] Japan .................. 58-139455
Mar. 13, 1984 [JP] Japan .................. 59-46529

[51] Int. Cl.$^4$ ............................................ C07C 99/00
[52] U.S. Cl. ..................................... 562/444; 562/435; 562/437; 549/444; 558/414
[58] Field of Search ............. 562/444, 435, 437; 549/444; 260/465 D

[56] References Cited

PUBLICATIONS

Shaw et al., J.A.C.S., vol. 75, pp. 3417–3419, (1973).
Hegedus et al., Chemica Acta, vol. 58, pp. 147–162, (1975).
Ogata et al., J. Org. Chem., vol. 38, pp. 3031–3034, (1973).
Eisele et al., Chem. Abst., vol. 83, #14852y, (1975).
Krasso, Chem. Abst., vol. 83, #10863m, (1975).

*Primary Examiner*—James H. Reamer
*Attorney, Agent, or Firm*—Fisher, Christen & Sabol

[57] ABSTRACT

In the production of a β-phenylserine by reacting glycine with a benzaldehyde in the presence of an alkali and treating the product with an acid, a novel process which comprises carrying out the reaction in a mixed solvent composed of water and a hydrophobic organic solvent. The presence of a phase transfer catalyst or a surface-active agent in this reaction system promotes the reaction and the β-phenylserine can be obtained in a high yield.

5 Claims, No Drawings

PROCESS FOR PRODUCTION OF β-PHENYLSERINE

BACKGROUND OF THE INVENTION

β-phenylserines are a kind of α-amino acids, and are useful not only as biologically active substances but also as intermediates for the production of β-phenylalanine derivatives.

There are prior methods of producing β-phenylalanine derivatives. For example, there is (1) a method which comprises reacting a copper complex of glycine with a benzaldehyde (for example, West German Pat. No. 960,722). The use of the copper salt, however, gives rise to a pollution problem, and the treatment of the waste water becomes troublesome. Moreover, this method generally has the defect of low yields. Another well known method is (2) a method of producing a β-phenylserine which comprises reacting glycine and a benzaldehyde in the presence of an alkali and then treating the product with an acid. For example, according to Kenneth N. F. Shaw and Sidney W. Fox, Journal of American Chemical Society, 75, 3419 (1953), β-phenylserine is obtained in a yield of 70% by reacting glycine and benzaldehyde in the presence of sodium hydroxide in water and treating the product with hydrochloric acid. This method, however, has a serious problem. As stated in the above-cited reference, the sodium salt of N-benzylidene-β-phenylserine, the reaction product of glycine and benzaldehyde, is temporarily precipitated, and the reaction mixture solidifies wholly. As a result, it becomes impossible to stir the reaction mixture mechanically. According to the reaction mechanism as shown in the reaction scheme (1) below, first 1 mole of glycine is condensed with 1 mole of benzaldehyde to form N-benzylidene-β-phenylserine. By treating the N-benzylidene-β-phenylserine with an acid, the desired β-phenylserine is formed.

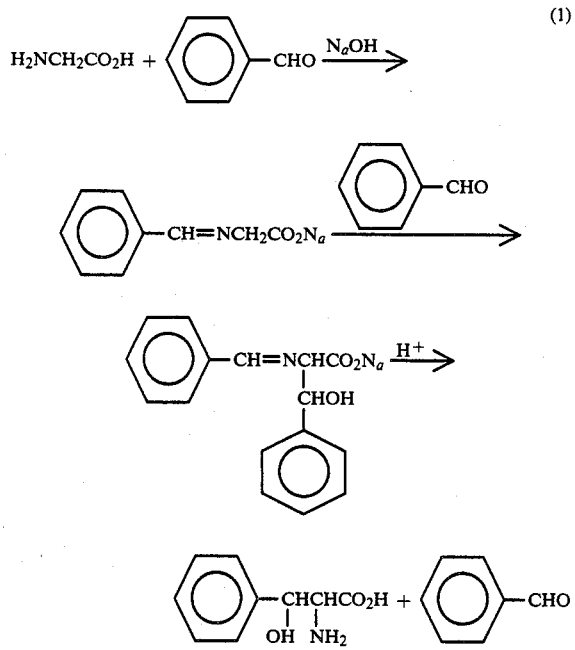

Accordingly, the reaction requires at least 2 moles of benzaldehyde per mole of glycine, and 1 mole of benzaldehyde is regenerated in the step of treating the intermediate product N-benzylidene-β-phenylserine. In the prior method, the β-phenylserine crystals are washed with alcohol to remove the adhering benzaldehyde in order to separate the benzaldehyde from the product (β-phenylserine). This causes the defect that the recovery of benzaldehyde from the filtrate left after separation of β-phenylserine becomes complex. The conventional methods of producing β-phenylserines have the various problems described above, and are not entirely satisfactory for industrial practice.

SUMMARY OF THE INVENTION

It is an object of this invention to provide an industrial process for producing β-phenylserines. More specifically, the object of this invention is to provide an industrial process for producing β-phenylserines in increased yields in which during the reaction of glycine with a benzaldehyde in the presence of an alkali, the flowability of the reaction mixture is improved and its stirring is very smooth.

This object is achieved by a process for producing a β-phenylserine which comprises reacting glycine with a benzaldehyde in the presence of an alkali, and treating the product with an acid, wherein the reaction is carried out in a mixed solvent composed of water and a hydrophobic organic solvent. The above object is also achieved with better results by performing the above reaction in the further presence of a phase transfer catalyst, or a surface-active agent, particularly a nonionic surface-active agent.

According to the process of this invention, the problem of stirring in aqueous solution in the aforesaid known methods can be solved. Furthermore, the β-phenylserine and the benzaldehyde can be separated from each other easily by dissolving the β-phenylserine as a mineral acid salt in water and the benzaldehyde in an organic solvent and separating the aqueous layer from the organic layer. In addition, the organic solvent layer so separated can be recycled without separating and recovering the benzaldehyde dissolved therein, by simply supplying an amount of the benzaldehyde which corresponds to that consumed by the reaction. This is also a great feature of the present invention.

When the surface-active agent is used in the reaction too, the organic solvent layer can be recycled without separating and recovering the surface-active agent dissolved therein.

Thus, the process for producing β-phenylserines in accordance with this invention not only solves the problems of the conventional techniques, but also enables the benzaldehyde and the surface-active agent as an optional component to be recycled efficiently, gives high reaction yields and ensures good efficiency. Hence, its industrial value is high.

DETAILED DESCRIPTION OF THE INVENTION

The benzaldehyde used as a starting material in the process of this invention is benzaldehyde (unsubstituted) or benzaldehyde having a substituent. Illustrative of the substituent of the substituted benzaldehyde are alkyl groups having 1 to 4 carbon atoms, alkoxy groups having 1 to 4 carbon atoms, aryloxy groups, a benzyloxy group, halogen atoms, a nitro group, a cyano group, a phenyl group and a methylenedioxy group. There is no particular limitation on the positions and numbers of the substituents.

Specific examples of the benzaldehyde include benzaldehyde, o-tolualdehyde, m-tolualdehyde, p-tolualdehyde, p-ethylbenzaldehyde, o-anisaldehyde, m-anisaldehyde, p-anisaldehyde, 3,4-methylenedioxybenzaldehyde, m-phenoxybenzaldehyde, m-benzyloxybenzaldehyde, p-benzyloxybenzaldehyde, 3,4-dibenzyloxybenzaldehyde, o-chlorobenzaldehyde, m-chlorobenzaldehyde, p-chlorobenzaldehyde, o-bromobenzaldehyde, m-bromobenzaldehyde, p-bromobenzaldehyde, 2,4-dichlorobenzaldehyde, 3,4-dichlorobenzaldehyde, o-nitrobenzaldehyde, m-nitrobenzaldehyde, p-nitrobenzaldehyde, p-cyanobenzaldehyde and p-diphenylaldehyde. The amount of the benzaldehyde used is at least 2 moles per mole of glycine, and there is no particular upper limit. Usually, the amount of the benzaldehyde may be 2.0 to 4.0 moles per mole of glycine.

The hydrophobic organic solvent used in the process of this invention may be any hydrophobic organic solvent which is inert to the reaction, and forms an aqueous layer and an organic layer. Specific examples include hydrocarbons such as xylene and ethylbenzene; halogenated hydrocarbons such as methylene chloride, dichloromethane, chloroform, carbon tetrachloride, dichloroethane, dichloroethylene, trichloroethane, trichloroethylene, chlorobenzene, o-dichlorobenzene and trichlorobenzene; alcohols such as 1-butanol, 2-butanol, isobutanol, 1-pentanol, 2-pentanol, 3-pentanol, 1-heptanol, 2-heptanol and 3-heptanol; ethers such as diethyl ether, dipropyl ether and diisopropyl ether; ketones such as methyl isobutyl ketone and diisobutyl ketone; and esters such as acetic acid esters and phosphoric acid esters. These are only illustrative examples.

These solvents are normally used singly, but a mixture of two or more of them may be used without any deleterious effect on the reaction. The amount of the organic solvent may be at least one which can dissolve the starting benzaldehyde at the reaction temperature. From the viewpoint of the reaction operation and the volume efficiency of the reaction, it is usually 0.3 to 20 times, preferably 0.5 to 10 times, the weight of the benzaldehyde.

According to this invention, the reaction is carried out in a mixed solvent composed of water and at least one of the hydrophobic organic solvents. There is no particular restriction on the ratio between water and the organic solvent in the mixture. Usually, it is sufficient that 20 to 500 parts by weight of the organic solvent is used per 100 parts of water.

The amount of water used in the reaction of this invention is at least 2 times, preferably 3 to 20 times, the weight of the starting glycine. When the amount of water exceeds 20 times the weight of the glycine, the yield of the reaction product is undesirably decreased.

The alkali used in the process of this invention is an alkali metal or alkaline earth metal hydroxide, such as lithium hydroxide, sodium hydroxide, potassium hydroxide, calcium hydroxide or magnesium hydroxide. The amount of the alkali may be above the theoretical amount, preferably at least 1.2 equivalents based on the starting glycine. There is no upper limit to the amount of the alkali. If, however, the alkali is used in too large an amount, the amount of the acid to be used at the time of acid treatment increases. Hence, usually, it is used in an amount of not more than 4 moles per mole of glycine.

Basically, the process of this invention comprises performing the reaction of glycine and the benzaldehyde in the presence of an alkali in a mixture of water and the hydrophobic organic solvent.

As required, a phase transfer solvent may be added to the reaction system. This promotes the reaction and the yield of the $\beta$-phenylserine increases. The effect of adding the phase transfer catalyst is particularly remarkable when the amount of the alkali used is not more than 1.5 equivalents based on the starting glycine.

Examples of the phase transfer catalyst include quaternary ammonium salts such as tetramethyl ammonium chloride, benzyl trimethyl ammonium chloride, benzyl triethyl ammonium chloride, benzyl tributyl ammonium chloride, tetrabutyl ammonium hydrogen sulfate and trioctyl methyl ammonium chloride; and quatenary phosphonium salts such as tetrabutyl phosphonium chloride, tetrabutyl phosphonium bromide, hexadecyl tributyl phophonium chloride and ethyl trioctyl phosphonium bromide. The amount of the phase transfer catalyst may be a catalytic amount. Specifically, the sufficient amount of the phase transfer catalyst is 0.01 to 2.0 g per 100 g of the starting glycine.

Instead of the phase transfer catalyst, a certain kind of surface-active agent may be added. The addition of the surface-active agent further improves the flowability of the reaction mixture in the reaction in the presence of alkali, and makes the stirring of the reaction mixture very smooth, thus increasing the operability. Moreover, this leads to an increase in the yield of $\beta$-phenylserine.

The surface-active agent may be an anionic, cationic or nonionic surface-active agent which does not impede the seperation of the aqueous layer and the organic solvent layer in the step of treating the reaction product with an acid which is to be practiced subsequent to the reaction in the presence of an alkali. The nonionic surface-active agent is especially effective. Specific examples include polyoxyethylene alkyl ethers, polyoxyethylenealkyl aryl ethers, sorbitan esters, sorbitan ester ethers and oxyethyleneoxy propylene block copolymers.

Usually, the surface-active agents are used singly, but a mixture of two or more of them may be used. If the amount of the surface-active agent is too small, its effect is not produced. If it is too large, the stirrability of the reaction mixture during the reaction rather gets worse. Usually, the suitable amount of the surface-active agent is 0.2 to 20% by weight, preferably 0.5 to 15% by weight, based on the starting glycine. The use of the nonionic surfactant brings about the advantage that no additional supply of the surface active agent is necessary when reusing the organic solvent layer obtained after the acid treatment. This is because generally, the nonionic surfactant is soluble in organic solvents but difficultly soluble in water.

In the process of this invention, there is no particular limitation on the sequence of charging the starting materials, the solvent, and the other materials. For example, an organic solvent having dissolved therein glycine, water and the aldehyde and optionally the phase transfer catalyst are charged, and with stirring, the alkali as a solid or an aqueous solution is charged or added dropwise to perform the reaction. Alternatively, it is possible to dissolve glycine in water and the alkali, and then add dropwise a solution of the benzaldehyde and the surface-active agent in an organic solvent to perform the reaction. Another method comprises charging or dropwise adding the alkali as a solid or aqueous solution into or to a mixture of glycine, water, the benzaldehyde, the organic solvent and the surface active agent, thereby performing the reaction. The reaction may be carried out at a temperature of 0° to 80° C. for 1 to 50 hours, preferably 10° to 60° C. for 3 to 30 hours. In this manner, the alkali metal or alkaline earth metal salt of the N-benzylidene-β-phenylserine is formed.

The reaction product without isolating the alkali metal or alkaline earth metal salt of the N-benzylidene-β-phenylserine is subsequently treated with a mineral acid to hydrolyze the N-benzylidene group and to form a β-phenylserine. More specifically, the mineral acid is added dropwise to the reaction mixture in an amount equal to or greater than the total equivalent of glycine and alkali used in the reaction, and the mixture is treated at 0° to 80° C., preferably 10° to 60° C. As a result, the N-benzylidene-β-phenylserine is easily hydrolyzed to give the corresponding β-phenylserine. The product dissolves as a mineral acid salt in the aqueous layer by the effect of the excess of the mineral acid. The acid used at this time is a mineral acid such as hydrochloric acid, sulfuric acid, phosphoric acid and boric acid. The amount of the mineral acid is one sufficient to convert the resulting β-phenylserine to its mineral acid salt, namely one equal to or greater than the total equivalent of the glycine and alkali used in the reaction. In the meantime, the excess of benzaldehyde not consumed by the reaction and the benzaldehyde grenerated by the hydrolysis of the N-benzylidene group by the acid treating operation dissolve in the organic solvent layer. After the acid treatment, the aqueous layer is separated from the organic solvent layer. The aqueous layer is neutralized with an alkali such as sodium hydroxide to precipitate crystals of the β-phenylserine. The crystals can be isolated by filtration. The organic solvent layer contains the unreacted benzalcehyde and the surface-active agent optionally added. The organic solvent layer can be recycled as such without recovering these materials by simply supplying an amount of the benzaldehyde which corresponds to that consumed by the reaction.

The following examples illustrate the present invention more specifically.

EXAMPLE 1

Water (400 g), 212 g of benzaldehyde and 120 g of toluene were added to 60 g of glycine. With stirring at 10° to 15° C., 177.8 g of 45% sodium hydroxide was added dropwise over the course of 2 hours. Then, the reaction temperature was gradually raised to 20° C., and the reaction was carried out at 20° to 25° C. for 20 hours. After the reaction, 292.0 g of 35% hydrochloric acid was added dropwise at a temperature of not more than 40° C., over 45 minutes. The mixture was further stirred at room temperature for 1 hour. After standing, the lower aqueous layer was separated and analyzed by high-performance liquid chromatography. The ratio of formation of β-phenylserine was 92.6% (based on glycine). The aqueous layer was neutralized to a pH of 6 with 45% sodium hydroxide, cooled to 0° to 5° C., stirred at the same temperature for 1 hour, filtered, washed with cold water, and then dried under reduced pressure at 50° C. to give 131.4 g of white crystals of β-phenylserine. The purity of this product analyzed by high-performance liquid chromatography was 90.5%. Differential thermal analysis showed that the product had one molecule of water of crystallization. The yield of the product (based on glycine) was 82.0%. Melting point: 198°–200° C. (decomposition).

Elemental analysis value (%) for $C_9H_{13}NO_4$

|  | C | H | N |
| --- | --- | --- | --- |
| Calculated: | 54.26 | 6.57 | 7.03 |
| Found: | 54.18 | 6.37 | 7.15 |

EXAMPLE 2

130.6 g of β-phenylserine was obtained by carrying out the same reaction as in Example 1 except that 89.0 g of benzaldehyde was additionally charged into the toluene solution of benzaldehyde recovered in Example 1.

EXAMPLE 3

129.5 g of β-phenylserine was obtained in the same way as in Example 1 except that 200 g of dichloroethane was used instead of toluene, 224 g of 50% potassium hydroxide was used instead of 45% sodium hydroxide, the reaction temperature was changed to 30°–35° C., and the reaction time was changed to 18 hours. The purity of the product was 90.9%. The yield based on glycine was 81.2%.

EXAMPLE 4

Glycine (60 g) and 48 g of sodium hydroxide were dissolved in 500 g of water. Then, 0.5 g of trioctylmethyl ammonium chloride was added, and with stirring at 25° to 30° C., a solution of 169.6 g of benzaldehyde in 150 g of toluene was added dropwise over the course of about 1 hour. The reaction was further carried out at 25° to 35° C. for 20 hours. After the reaction, 209 g of 35% hydrochloric acid was added dropwise at a temperature of less than 40° C. The mixture was stirred at room temperature for 1 hour. After standing, the lower aqueous layer was separated, neutralized with 45% sodium hydroxide to a pH of 6 at room temperature, stirred at 0° to 5° C. for 1 hour, filtered, washed with cold water, and dried to give 125.3 g of β-phenylserine. The purity of the product was 90.6%. The yield based on glycine was 78.3%.

EXAMPLES 5 TO 8

β-Phenylserine was synthesized from glycine and benzaldehyde in the same way as in Example 1 except that the organic solvent was changed as shown in Table 1. The results are shown in Table 1.

EXAMPLES 9 TO 13

Example 1 was repeated except that each of the substituted benzaldehydes shown in Table 2 was used instead of benzaldehyde. The results are shown in Table 2.

TABLE 1

Synthesis of β-phenylserine (glycine 60 g scale)

| | Organic solvent | | Water (g) | Benzaldehyde (g) | 45% NaOH (g) | Reaction conditions | | β-phenylserine | | |
| --- | --- | --- | --- | --- | --- | --- | --- | --- | --- | --- |
| Example | Kind | Amount (g) | | | | Temperature (°C.) | Time (hours) | Amount (g) | Purity (%) (*) | Yield (%) (**) |
| 5 | iso-Butanol | 150 | 400 | 212 | 150 | 30–35 | 16 | 118.2 | 98.9 | 73.4 |
| 6 | Diisobutylketone | 150 | " | " | " | " | " | 123.6 | 99.5 | 77.2 |

TABLE 1-continued

Synthesis of β-phenylserine (glycine 60 g scale)

| Example | Organic solvent Kind | Amount (g) | Water (g) | Benzaldehyde (g) | 45% NaOH (g) | Reaction conditions Temperature (°C.) | Time (hours) | β-phenylserine Amount (g) | Purity (%) (*) | Yield (%) (**) |
|---|---|---|---|---|---|---|---|---|---|---|
| 7 | Dipropyl ether | 150 | " | " | " | 20–25 | 20 | 129.4 | 99.6 | 80.9 |
| 8 | Tributyl phosphate | 200 | " | " | " | 10–15 | 24 | 125.9 | 99.2 | 78.3 |

(*): Purity as monohydrate
(**): Yield based on glycine

TABLE 2

Results of reaction with various substituted benzaldehydes (*)
(glycine 1.50 g (0.2 mole) scale)

| Example | Substituted benzaldehyde Kind | Amount (g) | Organic solvent Kind | Amount (g) | Reaction conditions Temperature (°C.) | Time (hours) | Substituted β-phenylserine Kind | Yield (% based on glycine) | Melting point (°C.) |
|---|---|---|---|---|---|---|---|---|---|
| 9 | p-Chlorobenzaldehyde | 61.8 | Toluene | 60 | 20–25 | 12 | β-(p-chlorophenyl)serine | 84.5 | 176–177 (decomp.) |
| 10 | m-Phenoxybenzaldehyde | 83.2 | " | 80 | 30–35 | 15 | β-(m-phenoxyphenyl)serine | 77.6 | 178–179 (decomp.) |
| 11 | m-Benzyloxybenzaldehyde | 89.0 | " | 90 | 30–35 | 15 | β-(m-benzyloxyphenyl)serine | 68.5 | 183–184 (decomp.) |
| 12 (**) | p-Benzyloxybenzaldehyde | " | Dichloroethane | 20 | 40–45 | 20 | β-(p-benzyloxyphenyl)serine | 60.5 | 188–190 (decomp.) |
| 13 (**) | 3,4-Dibenzyloxybenzaldehyde | 133.6 | Dichloroethane | 150 | " | " | β-(3,4-dibenzyloxyphenyl)serine | 62.8 | 178–180 (decomp.) |

(*): As the alkali 44.4 g of 45% sodium hydroxide was used. The amount of water used was 100 g.
(**): Trioctyl methyl ammonium chloride was used as a catalyst.

EXAMPLE 14

Example 1 was repeated except that the amount of sodium hydroxide was changed to 1.5 or 2.1 equivalents based on glycine, and the reaction was carried out in the presence of 0.5 g of trioctyl benzyl ammonium chloride as a phase transfer catalyst. The ratio of formation of β-phenylserine in the aqueous layer obtained by treating the reaction mixture with hydrochloric acid was measured. For comparison the reaction was carried out in the absence of the phase transfer catalyst. The results are shown in Table 3.

TABLE 3

| Amount of NaOH (moles per mole of glycine) | Phase transfer catalyst | Reaction conditions Temperature (°C.) | Time (hours) | Ratio of formation of β-phenylserine (mole % based on glycine) |
|---|---|---|---|---|
| 1.5 | Present | 25–35 | 20 | 86.8 |
| 1.5 | Absent | " | " | 77.6 |
| 2.1 | Present | " | " | 90.5 |
| 2.1 | Absent | " | " | 89.3 |

EXAMPLE 15

Glycine (30 g) was dissolved in 90 g of water and 88.9 g of 45% sodium hydroxide. While the solution was stirred at 25° C., a solution of 110.2 g of benzaldehyde and 3.0 g of Rheodol AO-15 (sorbitan ester-type) surfactant, a product of Kao Soap Co., Ltd.) in 150 g of toluene was added dropwise at 25° to 30° C. over the course of about 30 minutes, and the reaction was carried out at 30° to 35° C. for 8 hours. During the reaction, the reaction mixture could be stirred well. Thereafter, 146 g of 35% hydrochloric acid was added dripwise at a temperature of less than 40° C. over about 40 minutes, and the mixture was further stirred at room temperature for 1 hour. After standing, the lower aqueous layer was separated and analyzed by high-performance liquid chromatography. The ratio of formation of β-phenylserine based on glycine was found to be 95.7 mole%.

The aqueous layer was neutralized with 45% sodium hydroxide to a pH of 5.6 at room temperature, cooled to 0° to 5° C., stirred at the same temperature for 1 hour, then filtered, washed with cold water, and dried under reduced pressure at 60° to 70° C. to give 69.8 g of white crystals of β-phenylserine. The purity of the product analyzed by high-performance liquid chromatography was 90.6%. As a result of differential thermal analysis and the determination of moisture by the Karl-Fischer method, the product was found to contain 1 molecule of water of crystallization.

The yield of the isolated product was 87.2% (based on glycine), and the product had a melting point of 197° to 199° C. (decomp.).

Elemental analysis values for $C_9H_{13}NO_4$ (%)

|  | C | H | N |
|---|---|---|---|
| Found: | 54.10 | 6.78 | 6.81 |
| Calculated: | 54.26 | 6.57 | 7.03 |

COMPARATIVE EXAMPLE 1

In the procedure of Example 15, the organic solvent (toluene) and the surface-active agent were not used, and the reaction was carried out in water as a solvent. After the dropwise addition of benzaldehyde, the entire mixture solidified and could not be stirred.

EXAMPLE 16

44.5 g of benzaldehyde was freshly added to the toluene solution of benzaldehyde recovered in Example 15, and the same reaction as in Example 15 was carried out. The aqueous layer obtained after the acid treatment was analyzed by high-performance liquid chromatography. The ratio of formation of β-phenylserine was found to be 95.1% based on glycine. The flowability of the reaction mixture during the reaction was much the same as in Example 15.

EXAMPLES 17 TO 21

Example 15 was repeated except that the kind and amount of the surface-active agent were changed as shown in Table 4. The results are shown in Table 4 (glycine 30 g scale).

TABLE 4

| | Surface-active agent | | β-Phenylserine | | | |
|---|---|---|---|---|---|---|
| Example | Kind | Amount (g) | Value of analysis of the aqueous layer separated (mole % based on glycine) | Amount yielded (g) | Purity (%)[e] | Yield of the isolated product (%) |
| 17 | Rheodol AO-15 | 0.3 | 93.8 | 68.2 | 98.9 | 84.6 |
| 18 | Emulgen 404[a] | 1.5 | 93.6 | 67.4 | 99.3 | 84.0 |
| 19 | Emulgen 905[b] | 1.5 | 94.1 | 67.6 | 99.0 | 84.9 |
| 20 | Emulgen PP-150[c] | 1.5 | 92.6 | 67.5 | 98.6 | 83.5 |
| 21 | Rheodol TW-810[d] | 4.5 | 94.7 | 68.3 | 99.4 | 85.2 |

[a]polyoxyethylene oleyl ether produced by Kao Soap Co., Ltd.
[b]polyoxyethylene nonyl phenyl ether produced by Kao Soap Co., Ltd.
[c]oxyethylene/oxypropylene block copolymer produced by Kao Soap Co., Ltd.
[d]polyoxyethylene sorbitan monostearate produced by Kao Soap Co., Ltd.
[e]Purity as monohydrate

EXAMPLES 22 to 25

Example 15 was repeated except that the kind of the solvent, the amount of the solvent, the reaction temperature and the reaction time were varied as shown in Table 5. The results are shown in Table 5 (glycine 30 g scale; 15 g of Rheodol AO-15 was used as a surface-active agent).

127.2 g of benzaldehyde and 15 g of Rheodol AO-15 (sorbitan sesquioleate produced by Kao Soap Co., Ltd.) in 150 g of toluene was added dropwise at 10° to 15° C. over about 1 hour. The reaction was further carried out at the same temperature for 20 hours. After the reaction, 146 g of 35% hydrochloric acid was added dropwise at a temperature of less than 20° C. The mixture was further stirred at room temperature for 1 hour. After standing, the lower aqueous layer was separated and analyzed by high-performance liquid chromatography. The ratio of β-phenylserine formed in the aqueous layer was 86.0 mole% based on glycine.

The aqueous layer was neutralized with 45% sodium hydroxide to a pH of 5.6, cooled to 5° C., stirred at 0° to 5° C. for 1 hour, filtered, washed with cold water, and dried under reduced pressure at 70° C. to give 58.9 g of white β-phenylserine. The purity of β-phenylserine as its monohydrate was 98.4%. The yield of the isolated product was 72.7 mole% (based on glycine).

EXAMPLES 27 TO 30

TABLE 5

| | Organic solvent | | Reaction conditions | | β-Phenylserine | | |
|---|---|---|---|---|---|---|---|
| | | | | | Value of analysis of the aqueous layer separated (mole % based on glycine) | Amount of the isolated product (g) | Purity (%) (*) | Yield of the isolated product (mole % based on glycine) |
| Example | Kind | Amount (g) | Temperature (°C.) | Time (hours) | | | | |
| 22 | iso-Butanol | 150 | 20–25 | 10 | 86.5 | 61.5 | 98.6 | 76.1 |
| 23 | 1,2-Dichloroethane | 150 | 30–35 | 8 | 94.8 | 68.6 | 99.5 | 85.7 |
| 24 | Diisobutylketone | 120 | 45–50 | 5 | 91.7 | 66.9 | 99.3 | 83.4 |
| 25 | Xylene | 300 | 30–35 | 10 | 92.3 | 67.4 | 99.0 | 83.8 |

(*): Purity as monohydrate

EXAMPLE 26

Glycine (30 g) was dissolved in 90 g of water and 112.2 g of a 50% aqueous solution of sodium hydroxide. The solution was cooled to 10° C., and a solution of Example 15 was repeated except that each of the substituted benzaldehydes indicated in Table 6 was used instead of benzaldehyde. The results are shown in Table 6.

TABLE 6

| | Substituted benzaldehyde | | Organic solvent | | Reaction conditions | | Substituted β-phenylserine | | |
|---|---|---|---|---|---|---|---|---|---|
| Example | Kind | Amount (g) | Kind | Amount (g) | Temperature (°C.) | Time (hours) | Kind | Yield of the isolated product (mole % based on glycine) | Melting point (°C.) |
| 27 | p-chlorobenzaldehyde | 124.5 | toluene | 150 | 20–25 | 5 | β-(p-chlorophenyl)serine | 88.5 | 175.5–176.5 (decomp.) |
| 28 | m-phenoxybenzaldehyde | 174.2 | " | 200 | 30–35 | 8 | β-(m-phenoxyphenyl)serine | 82.1 | 178–179.5 (decomp.) |

TABLE 6-continued

| Example | Substituted benzaldehyde Kind | Amount (g) | Organic solvent Kind | Amount (g) | Reaction conditions Temperature (°C.) | Time (hours) | Substituted β-phenylserine Kind | Yield of the isolated product (mole % based on glycine) | Melting point (°C.) |
|---|---|---|---|---|---|---|---|---|---|
| 29 | m-benzyloxybenzaldehyde | 212 | 1,2-dichloroethane | 200 | 40–45 | 10 | β-(p-benzyloxyphenyl)serine | 66.5 | 188–190 (decomp.) |
| 30 | 3,4-dibenzyloxybenzaldehyde | 302 | 1,2-dichloroethane | 250 | " | " | β-(3,4-dibenzyloxyphenyl)serine | 65.4 | 179–180 (decomp.) |

What we claim is:

1. Process for producing a β-phenylserine, which comprises reacting glycine and a benzaldehyde in the presence of an alkali and then treating the reaction product with an acid, said reaction being carried out in a mixed solvent composed of water and a hydrophobic organic solvent selected from the group consisting of a hydrocarbon, a halogenated hydrocarbon, an alcohol, an ether, a ketone and an ester.

2. The process of claim 1 wherein the hydrophobic organic solvent is a hydrocarbon which is benzene, toluene, xylene or ethylbenzene, or a halogenated hydrocarbon which is methylene chloride, dichloromethane, chloroform, carbon tetrachloride, dichloroethane, dichloroethylene, trichloroethylene, chlorobenzene, dichlorobenzene or trichlorobenzene, or an alcohol which is 1-butanol, 2-butanol, isobutanol, 1-pentanol, 2-pentanol, 3-pentanol, 1-heptanol, 2-heptanol or 3-heptanol, or an ether which is diethyl ether, dipropyl ether or diisopropyl ether or a ketone which is methyl isobutyl ketone or diisobutyl ketone, or an ester which is an acetic acid ester or a phosphoric acid ester.

3. The process of claim 1 wherein the amount of the organic solvent is 20 to 500 parts by weight per 100 parts by weight of water.

4. Process for producing a β-phenylserine, which comprises reacting glycine and a benzaldehyde in the presence of an alkali and then treating the reaction product with an acid, said reaction being carried out in a mixed solvent composed of water and a hydrophobic organic solvent in the presence of a phase transfer catalyst, the hydrophobic organic solvent being selected from the group consisting of a hydrocarbon, a halogenated hydrocarbon, an alcohol, an ether, a ketone and an ester, and the phase transfer catalyst being selected from the group consisting of a quaternary ammonium salt and a quaternary phosphonium salt.

5. Process for producing a β-phenylserine, which comprises reacting glycine and a benzaldehyde in the presence of an alkali and then treating the reaction product with an acid, said reaction being carried out in a mixed solvent composed of water and a hydrophobic organic solvent in the presence of a surface-active agent, the hydrophobic organic solvent being selected from the group consisting of a hydrocarbon, a halogenated hydrocarbon, an alcohol, an ether, a ketone and an ester, and the nonionic surface-active agent selected from the group consisting of a polyoxyethylene alkyl ether, a polyoxyethylene alkyl aryl ether, a sorbitan ester, a sorbitan ester ether and an oxyethylene oxypropylene block copolymer.

* * * * *